(12) United States Patent
Koivukunnas et al.

(10) Patent No.: US 7,001,485 B2
(45) Date of Patent: Feb. 21, 2006

(54) ARRANGEMENT FOR MEASURING PROPERTIES OF A MOVING PAPER WEB

(75) Inventors: Pekka Koivukunnas, Järvenpää (FI);
Helena Leppäkoski, Järvenpää (FI);
Matti Kukkurainen, Tampere (FI);
Sakari Kauppinen, Kempele (FI)

(73) Assignee: Metso Automation Oy, Helsinki (FI)

( * ) Notice: Subject to any disclaimer, the term of this patent is extended or adjusted under 35 U.S.C. 154(b) by 189 days.

(21) Appl. No.: 10/047,054

(22) Filed: Jan. 14, 2002

(65) Prior Publication Data

US 2002/0104637 A1 Aug. 8, 2002

Related U.S. Application Data

(63) Continuation of application No. PCT/FI00/00650, filed on Jul. 14, 2000.

(30) Foreign Application Priority Data

Jul. 15, 1999 (FI) .................................... 991612

(51) Int. Cl.
*D21F 1/36* (2006.01)
*D21G 9/00* (2006.01)
*G01N 21/86* (2006.01)

(52) U.S. Cl. .................... 162/263; 162/198; 73/37; 73/159; 250/559.01

(58) Field of Classification Search ............... 162/252, 162/253, 263, 198, 199, 272, 193, 194, 361; 356/429, 431; 73/37.7, 73, 159; 250/559.01, 250/559.04

See application file for complete search history.

(56) References Cited

U.S. PATENT DOCUMENTS 3,713,966 A * 1/1973 Lippke ..................... 162/263
3,732,430 A 5/1973 Hujer et al.
3,855,524 A 12/1974 Crawford (Continued)

FOREIGN PATENT DOCUMENTS

WO WO-97/10383 3/1997

OTHER PUBLICATIONS

Copy of International Search Report for PCT/FI00/00650, completed Nov. 7, 2000.

(Continued)

*Primary Examiner*—Eric Hug
(74) *Attorney, Agent, or Firm*—Alston & Bird LLP

(57) ABSTRACT

An arrangement for measuring properties of a moving paper web. The arrangement comprises measuring means for measuring paper properties, in connection with which a plane-like support surface is arranged. The plane-like support surface supports the paper web and extends substantially over the whole width of the paper web in the cross-direction relative to the direction of travel of the paper web. An opening arrangement formed by at least one opening is arranged on the support surface for measuring properties of the paper web.

13 Claims, 2 Drawing Sheets

U.S. PATENT DOCUMENTS

| | | | |
|---|---|---|---|
| 3,868,851 A | | 3/1975 | Breyer |
| 3,992,100 A | | 11/1976 | Lodzinski et al. |
| 4,194,840 A | | 3/1980 | Lucas et al. |
| 4,311,037 A | * | 1/1982 | Gotchel et al. ............... 73/38 |
| 4,783,647 A | | 11/1988 | Wood |
| 4,789,431 A | * | 12/1988 | Typpo ...................... 162/263 |
| 4,877,485 A | * | 10/1989 | Carson ...................... 162/263 |
| 4,947,131 A | * | 8/1990 | Mayer et al. ............... 324/671 |
| 5,298,121 A | * | 3/1994 | Kilmister ................... 162/198 |
| 5,642,192 A | | 6/1997 | Gordon et al. |
| 5,745,244 A | * | 4/1998 | Svanqvist et al. .......... 162/263 |
| 5,928,475 A | * | 7/1999 | Chase et al. ................ 162/263 |
| 6,074,531 A | * | 6/2000 | Hultcrantz et al. ......... 162/263 |

OTHER PUBLICATIONS

Copy of Finnish Official Action for Appl. No. 991612, dated Mar. 14, 2000.

* cited by examiner

ARRANGEMENT FOR MEASURING PROPERTIES OF A MOVING PAPER WEB

CROSS-REFERENCE TO RELATED APPLICATIONS

This application is a Continuation of International Application PCT/FI00/00650 filed on 14 Jul. 2000, which designated the U.S. and was published under PCT Article 21(2) in English, and which is hereby incorporated herein in its entirety by reference.

BACKGROUND OF THE INVENTION

1. Field of the Invention

The invention relates to an arrangement for measuring properties of a moving paper web, which arrangement comprises measuring means for measuring properties of a paper web and a supporting member for supporting the paper web in connection with the measuring means.

Sections where the paper web is not supported by a wire, for example, are called open draws. Open draws cause flutter in the paper web, and particularly because of an increase in the speed of paper machines, open draws easily lead to web breaks, which cause considerable costs. Thus, the intention is to support the paper web in the paper machine as much as possible, for example with wires. However, during the manufacture, web properties are measured while the web is moving, which means that frequently, if required by the measuring method, for example, the measurements have to be performed without a wire that would support the web. Thus, open draws have to be used to perform the measurement.

2. Description of Related Art

U.S. Pat. No. 4,194,840 discloses a measuring device comprising a convex lens arranged to be in contact with the paper web to be measured. U.S. Pat. No. 3,992,100, in turn, discloses a measuring device comprising a spherical surface in contact with the paper web to be measured, which surface encircles the measuring window. In both of the above solutions, the means in contact with the paper web leave scratches and traces on the paper web. Further, although contacting the paper web, the measuring means are not able to support the paper web sufficiently.

WO Publication 97/10383 discloses one solution for supporting the web during measurement. In this solution, sensing means measuring properties of a paper web are positioned in a carriage arranged to traverse back and forth in the cross-direction relative to the direction of travel of the paper web. Plane-like members, such as a flexible belt, are arranged in connection with the carriage to support the paper web. The belt is attached to both edges of the measuring head, a roll being arranged on both sides of the wire, whereby the belt is uncoiled from the roll and coiled onto the roll according to the reciprocating motion of the measuring head. Thus, there is no belt or any other element supporting the paper web at the measuring windows, but inside a measuring beam in the lateral direction of the carriage, the paper web is supported during the whole of the measurement. Moreover, the WO publication discloses a solution for supporting a paper web after it has detached from the wire or felt before the measuring beam and after the measuring beam before the wire. The publication suggests the use of air blow pipes extending over the whole width of the web and plane-like members attached to them, which form a plane-like surface supporting the web. Flutter of the paper web can be decreased and the speed of the paper web increased by means of these solutions, since no open draws are required for the measurements. However, the solution is mechanically rather demanding to implement. Further, the solution cannot be used in measurements in which the measuring device requires a view over the whole width of the paper web.

BRIEF SUMMARY OF THE INVENTION

An object of the present invention is to provide an arrangement according to which properties of a paper web can be measured in such a way that the web is supported during the measurement in such a way that the supporting member does not considerably disturb the measurement or considerably affect the measurement results.

An arrangement according to the invention is characterized in that the supporting member is a plane-like support surface, which extends substantially over the whole width of the paper web in the cross-direction relative to the direction of travel of the paper web and on which an opening arrangement formed by at least one opening is arranged for measuring properties of the paper web.

The essential idea of the invention is that the arrangement comprises a measuring device, which is arranged in connection with the supporting member, i.e. the plane-like support surface. The plane-like support surface is substantially unmoving and has an opening arrangement covering substantially the whole width of the paper web. The idea of a preferred embodiment is that the support surface is arranged at least partly curved in such a way that the air brought along by the paper web forms an air layer between the plane-like support surface and the paper web. The idea of another preferred embodiment is that the opening arrangement is covered by transparent material.

An advantage of the invention is that the paper web can be supported in a simple and mechanically reliable way from the moment when the web detaches from the wire or felt, through the measuring beam and past the measuring sensors, until the web is again supported by the wire on the other side of the measuring beam. By means of the plane-like support surface, flutter of the paper web can be significantly decreased or even totally eliminated, whereby the structures required for measurement of paper properties do not impose any restrictions on the speed of the paper machine. When an air layer is formed between the support surface and the paper web, the plane-like support surface only subjects the paper web to the friction caused by air resistance. Thus, the support surface does not leave scratches or other traces on the paper web. By covering the openings with transparent material the measurements can be implemented through the openings, but the surface of the support surface is made very smooth.

In connection with this description, the term 'paper' also refers to paper board and tissue in addition to paper.

BRIEF DESCRIPTION OF SEVERAL VIEWS OF THE DRAWINGS

The invention is explained in greater detail in the attached drawings, of which.

DETAILED DESCRIPTION OF THE INVENTION

Figure 1:
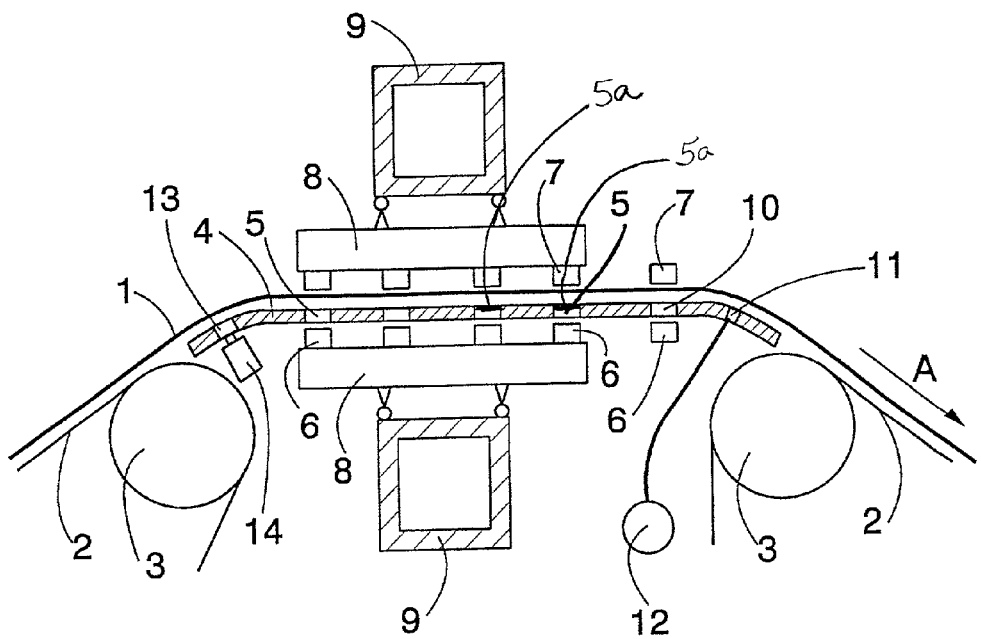
FIG. 1 schematically illustrates a side view of a cross-section of an arrangement according to the invention.

FIG. 1 illustrates an arrangement according to the invention seen from one side. In a paper machine, a paper web 1 is typically supported mainly by means of supporting wires 2, for example. The paper web 1 moves during the manufacture of paper in the direction of arrow A. The wire rotation of the supporting wires 2 is implemented by means of wire guide rolls 3. The paper web 1 is taken onto a plane-like or planar support surface 4 upon the supporting wire 2, being further led from the support surface 4 to the next supporting wire 2. The supporting wires 2 and the plane-like support surface 4 are arranged substantially in contact with each other, in other words in such a way that the paper web 1 is supported substantially all the time by means of either the supporting wire 2 or the support surface 4, i.e. there is no gap between the supporting wires 2 and the support surface 4, or the gap is so small that it does not considerably obstruct the travel of the paper web. The support surface 4 is arranged to extend substantially over the whole width of the paper web 1 in the cross-direction relative to the direction of travel A of the paper web. The plane-like support surface 4 is at least partly curved in such a way that the air brought along by the paper web 1 forms an air layer between the paper web 1 and the support surface 4 in such a way that the paper web 1 is substantially not in contact with the support surface 4. The support surface 4 has a smooth surface, whereby the formed air layer keeps the paper web 1 throughout at an equal distance from the surface of the support surface 4.

Openings 5 are arranged on the support surface 4, extending substantially from one edge of the paper web 1 to the other edge in the cross-direction relative to the direction of travel A of the paper web 1. The arrangement further comprises measuring sensors provided with a measuring transmitter 6 on the first side of the paper web 1 and a measuring receiver 7 at the corresponding point on the second side of the paper web 1, for the purpose of transmission measurement, for example. The measuring transmitter 6 and the measuring receiver 7 may be arranged in a measuring carriage 8. The measuring carriage 8, in turn, is arranged in relation to a measuring beam 9 to traverse back and forth in the cross-direction relative to the direction of travel of the paper web in a manner known perse. Owing to the openings 5, the measurement can be implemented through the support surface 4 in such a way that the support surface does not affect the measurement results. There may be several successive openings 5 on the support surface 4 in the direction of travel A of the paper, whereby measuring sensors measuring a single property or different properties may be positioned in connection with different openings 5. On the other hand, also in connection with one opening 5, several different sensors may be moved successively in the cross-direction of the paper, which allows measurement of different properties of the web, or, if desired, measurement of a single property through one opening 5. Properties measured from the paper may include moisture content, basis weight, paper thickness, etc.

Further, one or more measuring holes 10 may be arranged on the support surface 4. Properties of the paper web 1 can be measured at the measuring holes 10 as point measurement by means of measuring sensors remaining substantially unmoving. The temperature in the vicinity of the paper web 1, for example, can be measured through the measuring hole 10. Pressure-measuring holes 11 may also be arranged on the support surface 4, in connection with which holes pressure-measuring sensors 12 may be arranged. The pressure-measuring sensors 12 allow measurement of the pressure in the air layer between the paper web 1 and the support surface 4, and thus also definition of the tension profile of the paper web 1.

Air blow holes 13 may also be arranged on the support surface 4. Air can be blown by air blow means 14 through the air blow holes 13 between the plane-like support surface 4 and the paper web 1. By means of the air blow the tail threading of the paper web 1 can be improved and the formation of an air layer strengthened during the manufacture of paper.

A transparent cover 5a may be arranged on the openings 5. The transparent cover 5a enables measurement through the support surface 4 through the openings 5, but at the same time it removes the discontinuity points from the surface of the support surface 4, whereby the paper web 1 travels over the support surface 4 smoothly and without flutter. The transparent cover 5a may be glass or plastic, for instance.

Figure 2:
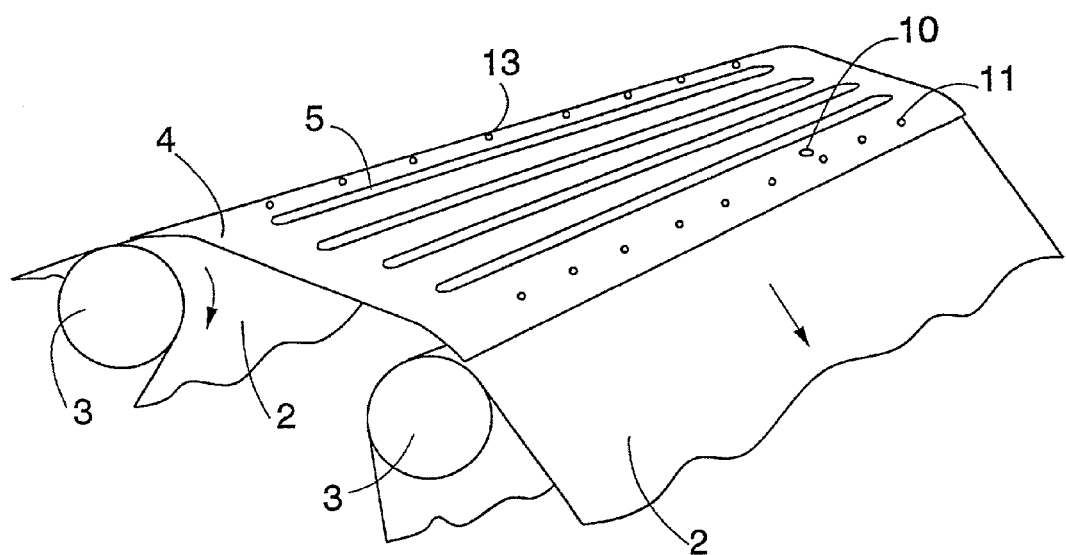
FIG. 2 illustrates a perspective view of a plane-like support surface according to the invention.

FIG. 2 illustrates the plane-like support surface 4 as a perspective view. The openings 5 cover substantially the whole width of the paper web, in other words their length may up to 10 meters, for example. The width of the openings 5 is very restricted relative to the length; they may be a few centimeters wide or narrower, for example. At the opening 5, a measuring sensor may be arranged which detects the whole width of the paper web 1 and is able to perform the measurement over the whole width of the paper web in one go.

Figure 3:
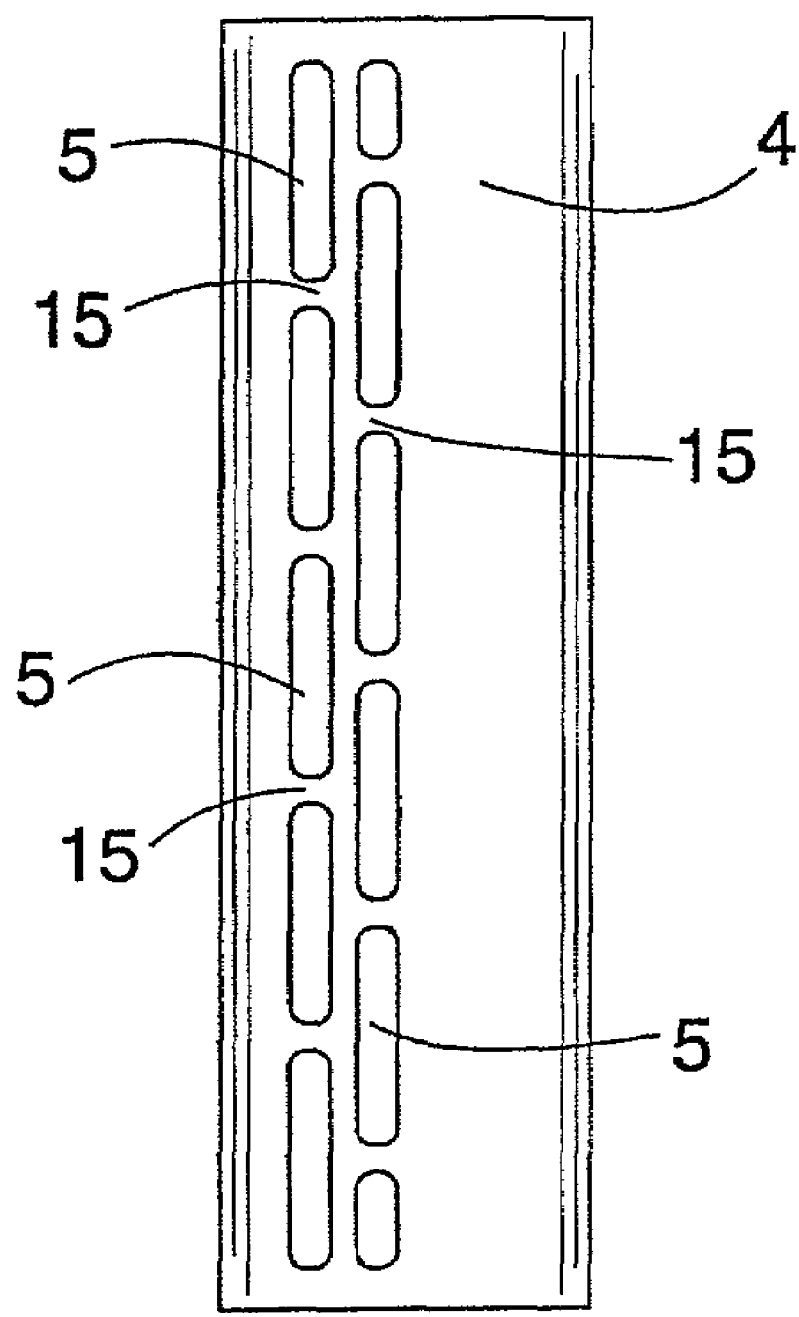
FIG. 3 schematically illustrates a top view of another plane-like support surface used in connection with the arrangement of the invention.

FIG. 3 illustrates a plane-like support surface 4, on which two opening arrangements are formed substantially over the whole width of the support surface 4 in the cross-direction relative to the direction of travel A of the paper web 1. In the embodiment shown in FIG. 3, however, one opening 5 does not extend from one edge of the paper web to the other, but there are necks 15 between the openings. Owing to the necks 15, a firm structure is achieved for the support surface 4. Naturally, properties of the paper web 1 cannot be measured at the point of the necks 15, at least not by means of transmission measurement. However, the necks 15 may be made so narrow that breaks in the measurements of the length of the necks 15 are so short that they do not considerably impair the measurement results and that a break in the measurement profile at the point of the necks 15 does not cause problems. The next openings 5 relative to the direction of travel A of the paper web 1 can, however, be arranged to stagger with the preceding openings 5 in such a way that at least at the preceding necks 15 there is an opening, whereby the points that could not be measured at the first necks 15 can be measured from other openings 5.

The drawings and the related description are only intended to illustrate the idea of the invention. The details of the invention may vary within the scope of the claims. Thus, the plane-like support surface 4 may be positioned either under or upon the moving paper web 1, depending on the measurement location and the properties to be measured. Further, the plane-like support surface 4 may be used not only in transmission measurement, but also in reflection measurement applications. All in all, the invention is particularly suitable for very fast paper machines that can produce even more than 2,200 meters of paper per minute.

That which is claimed:

1. An arrangement in a paper machine for measuring properties of a moving paper web having a predetermined width, which arrangement comprises:

measuring means for measuring properties of a paper web, and an unmoving plane-like support surface for supporting the paper web in connection with the measuring means, the plane-like support surface extending substantially over the whole width of the paper web in the cross-direction relative to the direction of travel of the paper web and defining at least one opening extending substantially over the whole width of the paper web, the measuring means being arranged to measure properties of the paper web through the plane-like support surface through the opening.

2. An arrangement according to claim 1, wherein the opening has a transparent cover.

3. An arrangement according to claim 1, wherein in connection with the plane-like support surface, air blow means are arranged for blowing air between the plane-like support surface and the paper web.

4. An arrangement according to claim 1, wherein the plane-like support surface is provided with at least one additional measuring hole for single measurements.

5. An arrangement according to claim 4, wherein in connection with the measuring hole, means are arranged for measuring the temperature of the paper web in the vicinity of the paper web.

6. An arrangement according to claim 1, wherein the measuring means are arranged to measure properties of the paper web by means of transmission measurement.

7. An arrangement according to claim 1, wherein at least one measuring means is arranged to be moved back and forth in the cross-direction relative to the direction of travel of the paper web.

8. An arrangement in a paper machine for measuring properties of a moving paper web having a predetermined width, which arrangement comprises:

measuring means for measuring properties of a paper web, and an unmoving plane-like support surface for supporting the paper web in connection with the measuring means in such a way that the paper web is substantially not in contact with the support surface, the plane-like support surface extending substantially over the whole width of the paper web in the cross-direction relative to the direction of travel of the paper web and defining at least one opening therein, the measuring means being arranged to measure properties of the paper web through the plane-like support surface through the opening.

9. An arrangement according to claim 8, wherein the plane-like support surface is at least partly curved in such a way chat the air brought along by the paper web forms an air layer between the paper web and the plane-like support surface.

10. An arrangement according to claim 9, wherein the plane-like support surface is provided with pressure-measuring holes, and that tile arrangement comprises means for measuring the pressure in the air layer for the purpose of defining the tension of the paper web.

11. An arrangement in a paper machine for measuring properties of a moving paper web having a predetermined width, which arrangement comprises:

measuring means for measuring properties of a paper web, the measuring means comprising at least one measuring transmitter and at least one measuring receiver, and an unmoving plane-like support surface for supporting the paper web in connection with the measuring means, the plane-like support surface extending substantially over the whole width of the paper web in the cross-direction relative to the direction of travel of the paper web and defining at least one opening therein, the measuring means being arranged to measure properties of the paper web through the plane-like support surface through the opening.

12. An arrangement in a paper machine for measuring properties of a moving paper web having a predetermined width, which arrangement comprises:

measuring means for measuring properties of paper web, and an unmoving plane-like support surface for supporting the paper web in connection with the measuring means, the plane-like support surface extending substantially over the whole width of the paper web in the cross-direction relative to the direction of travel of the paper web and defining at least two openings successively in the direction of travel of the paper web, the measuring means being arranged to measure properties of the paper web through the plane-like support surface through the opening.

13. An arrangement according to claim 12, wherein in connection with each opening, measuring means are arranged.

* * * * *

UNITED STATES PATENT AND TRADEMARK OFFICE
CERTIFICATE OF CORRECTION

| | |
|---|---|
| PATENT NO. | : 7,001,485 B2 |
| APPLICATION NO. | : 10/047054 |
| DATED | : February 21, 2006 |
| INVENTOR(S) | : Koivukunnas et al. |

It is certified that error appears in the above-identified patent and that said Letters Patent is hereby corrected as shown below:

Column 6,
Line 3, "chat" should read --that--.
Line 8, "tile" should read --the--.

Signed and Sealed this

Twelfth Day of September, 2006

JON W. DUDAS
*Director of the United States Patent and Trademark Office*